United States Patent [19]

Ludwigs

[11] Patent Number: 4,762,490
[45] Date of Patent: Aug. 9, 1988

[54] TOOTH SETTING AID ARRANGEMENT FOR POSITIONALLY CORRECTLY SETTING ARTIFICIAL TEETH IN A COMPLETE LOWER DENTURE

[76] Inventor: Horst Ludwigs, Lenbachstrasse 33, D-4800 Bielefeld 1, Fed. Rep. of Germany

[21] Appl. No.: 944,670

[22] Filed: Dec. 19, 1986

[30] Foreign Application Priority Data

Jun. 27, 1986 [DE] Fed. Rep. of Germany ... 8617182[U]

[51] Int. Cl.⁴ .............................................. A61C 11/00
[52] U.S. Cl. ........................................ 433/56; 433/55; 433/59
[58] Field of Search ...................... 433/56, 55, 54, 53, 433/57, 58, 59, 61, 62, 63, 64, 65, 67, 68, 72, 75

[56] References Cited

U.S. PATENT DOCUMENTS

| | | | |
|---|---|---|---|
| 2,571,280 | 10/1951 | Naggi | 433/63 |
| 2,618,068 | 11/1952 | Apple | 433/72 |
| 2,748,481 | 6/1956 | Glueck | 433/55 |
| 2,772,477 | 12/1956 | Miller | 433/55 |
| 3,277,576 | 10/1966 | Kraft | 433/53 |
| 3,414,977 | 12/1968 | Cayo | 433/57 |
| 3,693,257 | 9/1972 | Schreinemakers | 433/72 |

FOREIGN PATENT DOCUMENTS 2548532  1/1985  France .................. 433/56

*Primary Examiner*—John J. Wilson
*Attorney, Agent, or Firm*—Erwin S. Teltscher

[57] ABSTRACT

A tooth setting aid arrangement for use for positionally correctly setting artificial teeth in a complete lower denture on a lower jaw model in accordance with a Pound's line includes a holder which is positionally fixable with respect to the lower jaw model and is arched along an imaginary skullcap-shaped surface with a sagittal and transversal compensation curve, and two insert members which are pivotable and shiftable on the holder within the imaginary skullcap surface as well as arrestable in selected positions thereof relative to the holder for adjustment to the Pound's line. The holder is constituted by a bridge member which includes two plate-shaped bridge elements which are juxtaposed with one another and spaced from each other by a distancing element so as to bound an insertion space. Each of the insert members includes a straight portion and two arm portions which extend at an angle from one side of the straight portion. The insertion slot is dimensioned to receive the arm portions of either one of the insert members at a time, or of both of the insert members at the same time. Recessed head screws passing through the end portions of the bridge elements cooperate with knurled nuts for clamping the insert arms between the bridge portions upon tightening. The straight portions of the insert members have at least regions made of transparent material and provided with marking lines which are to be superimposed with the Pound's line.

29 Claims, 5 Drawing Sheets

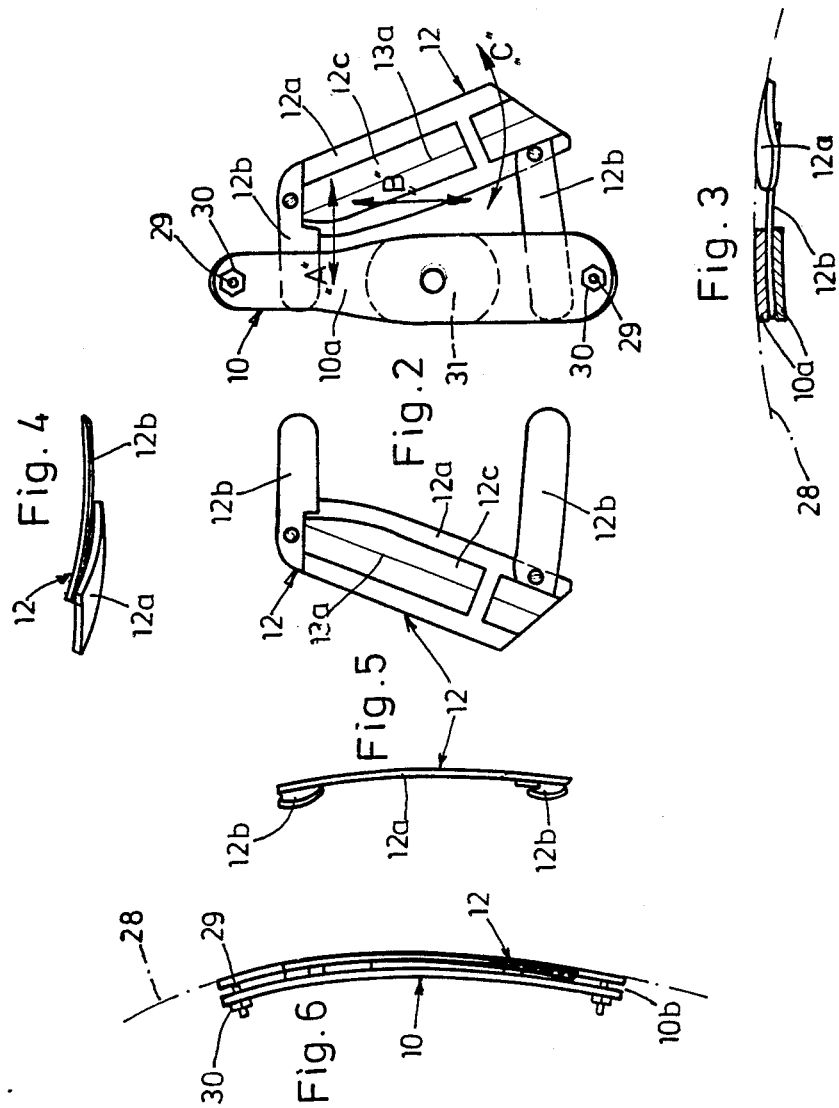

TOOTH SETTING AID ARRANGEMENT FOR POSITIONALLY CORRECTLY SETTING ARTIFICIAL TEETH IN A COMPLETE LOWER DENTURE

BACKGROUND OF THE INVENTION

The present invention relates to the field of dentistry in general, and more particularly to a tooth setting aid arrangement for use in a positionally correct setting of artificial teeth in a complete lower denture.

It is well known to those active in the field of dentistry that, when it is desired to achieve proper operation of a lower denture, the artificial teeth of the lower denture must be precisely positionally set along an arcuate course or in accordance with a so-called Pound's line which was named after the late Dr. Earl Pound. Currently, this is a very time-consuming and laborious operation so that, more often than not, the proper bite is achieved on a trial-and-error basis in that excessive material is removed from the artificial teeth during the fitting of the denture to the patient. This, however, is also very time consuming.

SUMMARY OF THE INVENTION

Accordingly, it is a general object of the present invention to avoid the disadvantages of the prior art.

More particularly, it is an object of the present invention to provide an arrangement for setting the teeth of a lower denture, which arrangement does not possess the drawbacks of the known arrangements of this type.

Still another object of the present invention is to devise an arrangement of the type here under consideration which renders it possible to set the teeth in accordance with the Pound's line in a very simple manner.

It is yet another object of the present invention to design the above arrangement in such a manner as to provide a high precision of the positioning of the artificial teeth in accordance with the Pound's line.

A concomitant object of the present invention is so to construct the arrangement of the above type as to be relatively simple in construction, inexpensive to manufacture, easy to use, and yet reliable in operation.

In keeping with these objects and others which will become apparent hereafter, one feature of the present invention resides in a tooth setting aid arrangement for use in a positionally correct setting of artificial teeth in a complete lower denture on a lower jaw model in accordance with a Pound's line, which arrangement comprises a holder which is positionally fixable with respect to the lower jaw model and is arched along an imaginary skullcap-shaped surface with a sagittal and transversal compensation curve; and two insert members which are pivotable and shiftable on the holder within the imaginary skullcap surface as well as arrestable in selected positions thereof relative to the holder for adjustment to the Pound's line.

As a result of the construction of the arrangement of the present invention in the manner described so far, it is possible to correctly position the artificial teeth of the lower denture, especially as far as their inclinations are concerned, on the basis of the compensation curve that is formed by the tooth setting aid arrangement, in accordance with the Pound's line which is exactly defined with respect to the given values of the lower jaw model by means of the positionally adjusted insert members.

It is advantageous when, in accordance with the present invention, the holder is constructed for alternate releasable insertion of only one of the insertion members at a time in such a manner that the one insert member is pivotable and shiftable relative to the holder within the imaginary skullcap surface curvature as well as arrestable in a selected position thereof relative to the holder for adjustment to the respective associated left or right portion of the Pound's line. However, it is also proposed by the present invention to construct the holder in such a manner as to be suited for simultaneous releasable insertion of both of the insertion members so that the two insert members are pivotable and shiftable relative to the holder within the imaginary skullcap surface curvature as well as arrestable in selected positions thereof relative to the holder for adjustment of each of the insert members to the respective associated left or right portion of the Pound's line. As a result of this simple and arbitrary adjustment of the positions of the insert members relative to the holder, it is possible to achieve an exact adjustment to or alignment with the Pound's line.

According to an advantageous aspect of the present invention, the holder is constituted by an elongated bridge member including two plate-shaped bridge elements which are juxtaposed with one another, connected to each other, and spaced from one another to jointly bound an insertion slot for the insert members. Each of the insert members has at least one insert arm, and the holder further includes a plate-shaped distancing member interposed between the bridge elements at a central longitudinal region of the latter for forming the insertion slot between the bridge elements and having a height corresponding either to the thickness of the insert arm for alternate insertion of only one of the insert members at a time, or to the combined thickness of the insert arms of the two insert members for simultaneous insertion of both of the insert members. In the latter case, the distancing member may include two superimposed plate-shaped distancing elements. Advantageously, the holder further includes at each of the longitudinal ends of the bridge member a knurled nut and a recessed head screw which threadedly engages the knurled nut for clamping the insert arm of at least one of the insert members between the bridge elements, the screws having respective heads which extend flush with a lower side of the bridge member. By providing the aforementioned screws, it is possible to securely arrest the insert members in their respective adjusted positions.

The tooth setting aid arrangement is advantageously to be used in conjunction with an articulator apparatus, in which event there is further provided an adapter for mounting the holder on the articulator apparatus, and a recessed head screw which mounts the holder from below on the adapter and has a recessed head which extends flush with a lower side of the holder. It is further advantageous when each of the insert members includes an elongated straight portion which is adjustable to the Pound's line, and two insert arms each extending at an angle from one end of the straight portion and clampingly received in the insertion slot of the bridge member for infinite shifting and pivoting in the slot.

At least the straight portion of each of the insert members advantageously includes at least a region of a transparent material, and a marking line which extends in the longitudinal direction of the straight portion and which is to be brought into registry with the Pound's line is provided at a lower side of this transparent region. The transparent region may be constituted by a strip of a synthetic plastic material supported on the remainder of the straight portion. However, it is also proposed by the present invention to make the straight portion in its entirety of a transparent synthetic plastic material. The marking line may be constituted by at least one of a color line, groove, bulge and the like. By providing the marking line on the transparent region of the insert members, it is possible to accurately determine the positionally correct setting of the artificial teeth with respect to the lower denture model ridge. The holder may also be provided with a marking line, this additional marking line extending along a longitudinal axis of the holder. Even this additional marking line may be constituted by at least one of a color line, groove, bulge and the like.

The tooth setting aid arrangement of the present invention may be used to advantage with an articulator apparatus including a support bolt, in which case there may be further provided a rigid adapter secured to the holder and so mounted on the articulator apparatus as to determine a defined chewing plane of the arrangement with the support bolt of the articulator apparatus. When the articulator apparatus includes an adjustment pin with a point mounted on the support bolt, it is proposed in accordance with an additonal facet of the present invention to provide a height-adjustable adapter connected to the holder and so mounted on the articulator apparatus as to be adjustable by the adjustment pin to a chewing plane. The tooth setting aid arrangement, in conjunction with an articulator apparatus, is thus constructed for a precise and convenient operation as well as for an unobjectionable fabrication of complete lower jaw dentures.

According to an additional concept of the present invention, there is further provided at least one tooth templet including a pseudo tooth having a mesial edge, and an insertion arm connected to the pseudo tooth and releasably mountable for movement in the sagittal direction and arrestable on the holder so that the mesial edge of the pseudo tooth is aligned with a central line of the holder. Advantageously, the mesial edge constitutes an adjustment surface for one of the left and right teeth 1. The insertion arm of the tooth templet advantageously extends in one of the rightward and leftward directions from the pseudo tooth for use in the respective one of rightward and leftward applications. It is also advantageous when the central line, which extends along the axis of symmetry of the denture, is formed by a groove-shaped recess which is milled into the lower bridge strip of the holder. The insertion arm of the tooth templet may include an abutment edge which cooperates with a longitudinal abutment edge of the holder to limit the insertion depth of the insertion arm and to hold the mesial edge in alignment with the central line in any adjusted position of the tooth templet in the sagittal direction. The insertion arm extends at an angle, preferably substantially at a right angle, with respect to the mesial edge and is insertable between the bridge strips of the holder, and there is further provided a screw including a knurled nut and operative for arresting the insertion arm in any position thereof which is infinitely adjusted in the sagittal direction. The tooth templet is advantageously of one piece and is made of a metallic material, of a synthetic plastic material, or the like.

BRIEF DESCRIPTION OF THE DRAWING

The present invention will be described below in more detail with reference to the accompanying drawing in which:

FIG. 2 is a top plan view of a skullcap-curved holder and two insert members of the tooth setting aid arrangement of FIG. 1, with one of the insert members being secured in position on the holder while the other insert member is disassembled from the holder;

FIG. 3 is a partially sectioned front elevational view of the holder with the insert member of FIG. 2;

FIG. 4 is a front elevational view of one of the insert members of FIG. 2;

FIG. 5 is a side elevational view of one of the insert members of FIG. 2;

FIG. 6 is a side elevational view of the holder with the insert member of FIG. 2;

DETAILED DESCRIPTION OF THE PREFERRED EMBODIMENT

Figure 1:
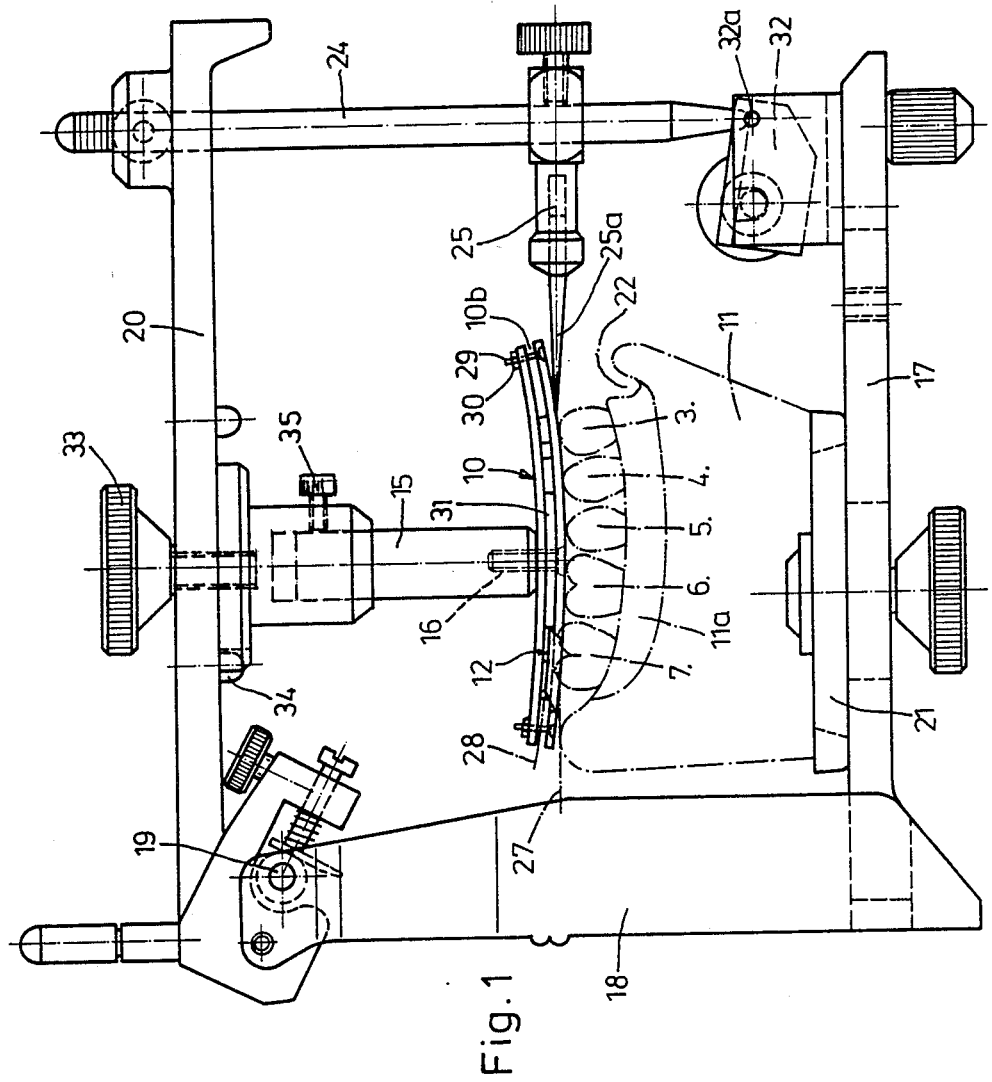
FIG. 1 is a side elevational view of an articulator apparatus for the fixation of lower jaw models, with a tooth setting aid arrangement of the present invention for complete lower jaw dentures being mounted on a hinged articulator apparatus arm shown in its position of use.

Referring now to the drawing in detail, and first to FIG. 1 thereof, it may be seen that it depicts a tooth setting aid arrangement for use in a positionally correct setting of artificial teeth in a complete lower denture. As seen especially in FIG. 9, the reference numerals 1 to 7 have been used to identify the first to seventh teeth on each side of the denture, counting from the front center, while the reference numeral 8. designates a so-called wisdom tooth.

The aforementioned arrangement includes a tripartite cap member which includes a holder 10 that is positionally fixable with respect to a lower jaw model 11, and two insert members 12. The holder 10 is arched along an imaginary skullcap-shaped surface so that the holder 10 has a sagittal and transversal compensation curve 28, while the insert members 12 are pivotable and shiftable within the imaginary skullcap (skullcap curvature/skullcap plane) as well as arrestable in selected positions thereof relative to the holder 10 for adjustment to the so-called Pound's lines 13.

The holder 10 is constituted by an elongated bridge member which is curved in its longitudinal and transverse directions in accordance with the aforementioned imaginary skull cap surface and which includes two elongated substantially coextensive bridge strips 10a that are maintained at a predetermined spacing from one another by means of a distancing element 31 and are connected with one another at each of their respective ends by a screw 29 having a recessed head and threadedly engaging a knurled nut 30. The bridge strips 10a bound between themselves an insertion slot 10b which extends over the entire bridge width and, except for the space occupied by the distancing element 31, over the entire bridge length.

The distancing element 31 is constituted by a distancing plate which extends over the central longitudinal region of the holder 10. A screw 16 having a recessed head passes from below through the two bridge strips 10a and through the distancing element 31. The screw 16 connects the tooth setting aid arrangement to an adapter 15. The adapter 15, in turn, mounts the tooth setting aid arrangement on an articulator device which is shown in detail in FIG. 1 of the drawing.

The two recessed head screws 29 also pass through the bridge strips 10a from below. The end surfaces of the recessed heads of all three screws 16 and 29 are flush with the lower effective skullcap-shaped surface curvature, so that they are free of any interfering effect.

Each of the two insert members 12 consists of an elongated straight portion 12a and two insert arms 12b each of which extends from a common lateral marginal portion of the straight portion 12a at a predetermined angle with respect to the longitudinal direction of the straight portion 12a. The straight portion 12a and the insert arms 12b are constituted by plate-shaped or strip-shaped parts and are arched in the sagittal and transversal directions in correspondence with the aforementioned imaginary skullcap-shaped surface. The insert arms 12b may be connected to the straight portion 12a, and especially to an upper surface region thereof, by gluing, or by means of rivets, screws or the like, or they may be made of one piece with the straight portion 12a. The insert arms 12b of each of the insert members 12 extend from one side of the holder 10 into the insertion slot 10b of the holder 10. During the adjustment to the Pound's line 13, the insert arms 12b of one or both of the insert members 12 are inserted into the holder 10. When only one of the insert members 12 is used at first during such adjustment, this first insert member 12 is removed from the holder 10 after the adjustment to the Pound's line 13 and after the setting of the teeth 3 to 7 at one side of the denture, and then the second insert member 12 is inserted into the holder 10 and the same procedure as before is performed at the other side of the denture.

The insertion slot 10b and the insert arms 12b are so coordinated with one another that a clamping effect is encountered in the inserted position. This clamping effect may then be further enhanced or strengthened by the screws 16 during their tightening. As a result of the utilization of knurled nuts 30, excessive tightening of the nut/screw combinations 30, 16 is prevented and use of a tool for tightening the nut 30 is excluded.

It is currently preferred to make the straight portion 12a of the insert member 12 of a transparent synthetic plastic material, and to provide at the lower side of the straight portion 12a a straight-line line marking 13a, such as a colored line, groove, protrusion or the like. In this case, the straight portion 12a can be exactly adjusted to the Pound's line 13 by using this line marking 13a. However, the straight portion 12a may also be only partially transparent, as indicated in FIG. 2 of the drawing. Under these circumstances, the straight portion 12a is provided with a window into which there is inserted a transparent part 12c which is provided with the line marking 13a.

Notwithstanding the above, the straight portion 12a can also be made of an opaque material. In this event, the inner longitudinal edge of the straight portion 12a constitutes a tooth guidance edge which is to be adjusted in accordance with the Pound's line 13.

As shown in FIG. 2 of the drawing, when the insert arms 12b of the respective insert member 12 are inserted into the insertion slot 10b of the holder 10, the insert member 12 is steplessly or infinitely shiftable in lateral directions indicated by an arrow "A" as well as in longitudinal directions identified by an arrow "B", and is also steplessly or infinitely pivotable in the directions of an arrow "C", so that an individual adjustment of the position of each insert member 12 relative to the holder 10 is rendered possible. Herein, however, the insert member 12 is situated, in each of its adjusted positions relative to the holder 10, always within the region bounded by the imaginary skullcap-shaped surface, that is, the insert member 12 is always moved during its positional adjustment relative to the holder 10 only within the skullcap-shaped surface curvature.

The holder 10 and the two inserts 12 may be made of metal, such as light metal, in which case they would be opaque, or they may be provided with a transparent region for the marking 13a, or they may be made of a transparent synthetic plastic material.

The straight portion 12a of the respective insert member 12 and the insert arms 12b which are either connected to the straight portion 12a or are of one piece therewith, preferably have a rectangular basic outline; however, they also may have any other suitable basic outline.

In FIGS. 1, 3 and 6, the holder 10 is constructed for the reception of only one of the insert members 12. Consequently, the distancing element 31 has a height which corresponds to the thickness of the insert arms 12b, and the height of the slot 10b is determined accordingly. In this particular construction, one insert member 12 is inserted first and aligned with the Pound's line 13. This insert member 12 is subsequently removed, after the setting of the teeth 3 to 7, and the other insert member can then be inserted and used for the oppositely situated row of teeth 3 to 7.

Figure 7:
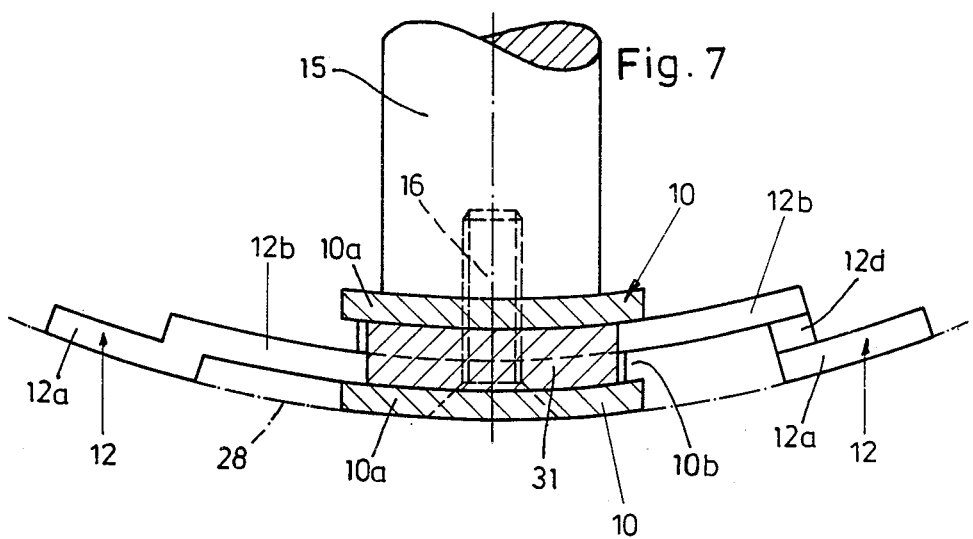
FIG. 7 is a partially sectioned front elevational view of the holder mounted on an adapter and simultaneously holding both of the insert members of FIG. 2.
Figure 8:
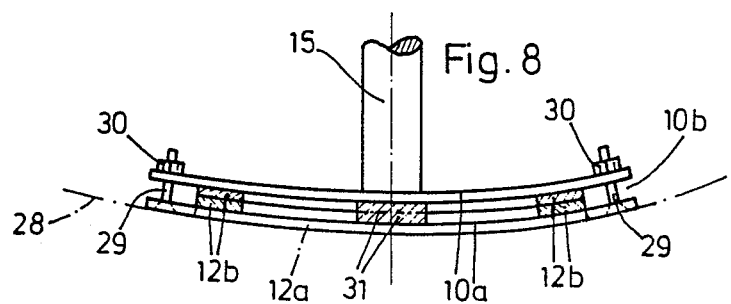
FIG. 8 is a partially sectioned front elevational view of the holder with the insert members in accordance with FIG. 7.

FIGS. 7 and 8 show a construction suited for the simultaneous insertion of both of the inserts 12. In this instance, the height of the distancing element 31 corresponds to twice the thickness of the insert arms 12. The distancing element 31 is constituted by a plate-shaped part or as two superimposed plate-shaped parts, so that the slot 10b renders it possible to insert both of the insert members 12 thereinto. In this case, the arms 12b of the two insert members 12 are located on top of one another.

It is currently preferred for the distancing element 31 to be constituted by two equally thick plate-shaped parts the thicknesses of which correspond to those of the insert arms 12b. In this instance, the holder 10 can be used as desired by using only one or both of the plate-shaped parts of the distancing element 31 either for an alternative one-sided, or for a simultaneous two-sided, insertion of the two insert members 12.

FIG. 1 further shows the previously mentioned articulator apparatus which is generally of a known construction and which is designed for the reception and mounting of the tooth setting aid arrangement according to the present invention. The articulator apparatus includes a substantially flat base plate 17, on which there are supported vertical columns 18. A hinged arm 20 for the mounting of the tooth setting aid arrangement by means of the adaptor 15 is held between the upper regions of the columns 18 for pivoting about a horizontal axis 19.

The lower jaw model 11 is supported on the base plate 17 by means of a pedestal plate 21 in such a manner as to be properly aligned relative to the articulator apparatus as far as a symphysis line 22 and trigona 23 are concerned.

A support bolt 24 carrying an adjustment pin 25 for the chewing plane 27 is mounted on the hinged arm 20. In the downwardly pivoted position of the hinged arm 20, which is shown in FIG. 1 of the drawing, the adjustment pin 25 holds the tooth setting aid arrangement at the correct bite elevation.

The support bolt 24 is mounted on the hinged arm 20 for adjustment of its elevation above the base plate 17 and it is supported on an adjustment table 32 of the base plate 17 which is pivotable about a horizontal pivoting axis 32a. The longitudinal axis of the support bolt 24 is aligned with the pivoting axis 32a.

The bite plane 27 of the tooth setting aid arrangement 10, 12 is fixed in such a manner that the adapter 15 by itself constitutes a rigid unit and its elevation with respect to the articulator apparatus being used is defined, so that the correct bite plane 27 is always available after the downward pivoting of the hinged arm 20 with the adapter 15 and the tooth setting aid arrangement 10, 12.

The adapter 15 is dismountably connected to the hinged arm 20 by means of a knurled screw 33 and it is held against turning relative to the hinged arm 20 by at least one projection 34 of the hinged arm 20 which engages in the adapter 15.

However, the elevation of the bite plane 27 above the base plate 17 can also be adjusted by so constructing the adapter 15 as to be height-adjustable. In the illustrated construction, the adapter 15 consists of two parts which are telescopically received in one another for shifting relative to each other. An arresting screw 35 arrests the adapter 15 at the desired elevation.

The adjustment pin 25 has a pointed portion 25a and is mounted on the vertical support bolt 24 so as to be prevented from turning about the support bolt 24, to be vertically shiftable on the support bolt 24, and to be arrestable in any desired vertical position thereof. The support bolt 24 is provided at the elevation of the imaginary bite plane 27 with a marking to which the adjustment pin 25 is adjusted. Then, the pointed portion 25a of the adjustment pin 25 lies at the bite plane 27 and thus at the incisal point.

Furthermore, the adjustment pin 25 always points in the longitudinal direction of the holder 10 and its pointed portion 25a lies at the longitudinal axis 36 of the holder 10 which is indicated by a central line provided on the holder 10.

For the adjustment of the adapter 15 to the bite plane 27, the hinged arm 20 is pivoted downwardly and the holder 10 descends onto and abuts the pointed portion 25a of the adjustment pin 25. As a result of this abutment, the holder 10 has the correct desired elevational position. Now, the adapter 15 can be fixed or arrested by the tightening of the arresting screw 35 and the tooth setting aid arrangement 10, 12 is now exactly at the elevation of the bite.

The longitudinal axis 36 of the holder 10 extends at the longitudinal axis of the articulator arrangement, so that the central axis of the jaw remains recognizable even after the removal of the adjustment pin 25, in that the user is able to take bearings on the basis of the central line 36 which is provided on the holder 10.

Figure 9:
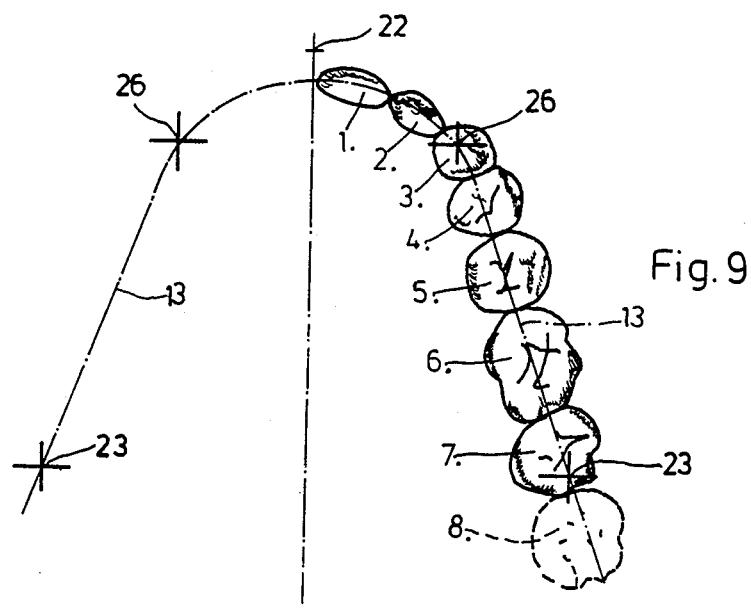
FIG. 9 is a diagrammatic top plan view of the two Pound's lines of the lower jaw with a tooth row provided on only one half of the lower jaw.

FIG. 9 shows a diagrammatic top plan view of a lower jaw with a row of teeth 1 to 8. It is shown here that the Pound's lines 13 extend between respective corner tooth points 26 and the associated trigona 23.

The succession of operations performed during the setting of the teeth of the complete lower jaw denture by means of the tooth setting aid arrangement of the present invention in conjunction with the above-discussed articulator apparatus is as follows:

1. The lower jaw model 11 is inserted into the articulator arrangement and mounted thereon by means of the pedestal plate 21 in such a manner that the significant points, lines and planes, particularly the symphysis line 22, the trigonal points 23 and the bite plane 27, assume their correct desired positions relative to the articulator apparatus.

2. The hinged arm 20 with the tooth setting aid arrangement 10, 12 mounted thereon by means of the adapter 15 is pivoted downwardly into its position of use which is illustrated in FIG. 1 of the drawing, so that the tooth setting aid arrangement 10, 12 is held at the desired elevation above the base plate 17 either by means of the adjustment screw 24 and the adapter 15 which is rigid in this instance, or by means of the adjustment pin 25 and the elevationally adjustable and arrestable adapter 15, and so that the height with respect to the bite plane 27 of the teeth 3 to 7 to be set is determined in a defined manner.

3. The trigonal points 23 and the corner tooth points 26 are marked on a ridge 11a of the model 11.

4. Subsequently, the Pound's line 13, which is represented at the lower side of the straight portion 12a, is to be brought into alignment in the vertical direction with the markings 23 and 26 that are provided on the ridge 11a of the lower jaw model 11; this is accomplished by the shifting and pivoting of the single insert member 12 or of both insert members 12.

5. The arresting of the positionally adjusted insert member 12 or insert members 12 is accomplished either automatically by the clamping of the insert arms 12a in the insertion slot 10b, or by the tightening of the knurled nuts 30.

6. Now, the teeth 1 to 7 can be set.

7. Using one of the insert members 12, the row of teeth 3 to 7 is set on one side of the jaw model 11; thereafter, either the one insert member 12 is removed from, and the second insert member 12 is mounted on the holder 10, whereupon the same setting procedure is repeated with another tooth row at the other side of the jaw model 11, or, when both of the insert members 12 are simultaneously secured in their respective positions on the holder 10, then both of the aforementioned tooth rows can be set in one and the same operation.

The teeth 1 to 7 are situated at the sagittal and also transversal compensation curve 28, whose curved shape is also shared by the tooth setting aid arrangement 10, 12, and which intersects the imaginary chewing plane 27 at the elevation of the tooth 3. as well as the transition region between the teeth 6 and 7.

As a result of the provision of the line 13a at the underside of the transparent insert members 12 or straight portions 12a, the effect of the light refraction is circumvented and, consequently, an optimally correct adjustment from above is rendered possible.

The adjustment of the lower jaw teeth 3 to 7 occurs in accordance with the adjusted Pound's line and, therefore, satisfies important basic preconditions for the function of the denture to be produced.

As shown in FIG. 7 of the drawing, when both of the insert members 12 are to be simultaneously inserted into the holder 10, a spacer 12d is inserted between the straight portion 12a and the insert arm 12b of one of the insert members 12, so that the insert arms 12b of the two insert members 12 are juxtaposed with one another in the mounted position of the two insert members 12 on the holder, and the two straight portions 12a extend within the same skullcap-shaped arched surface 28.

Figure 10:
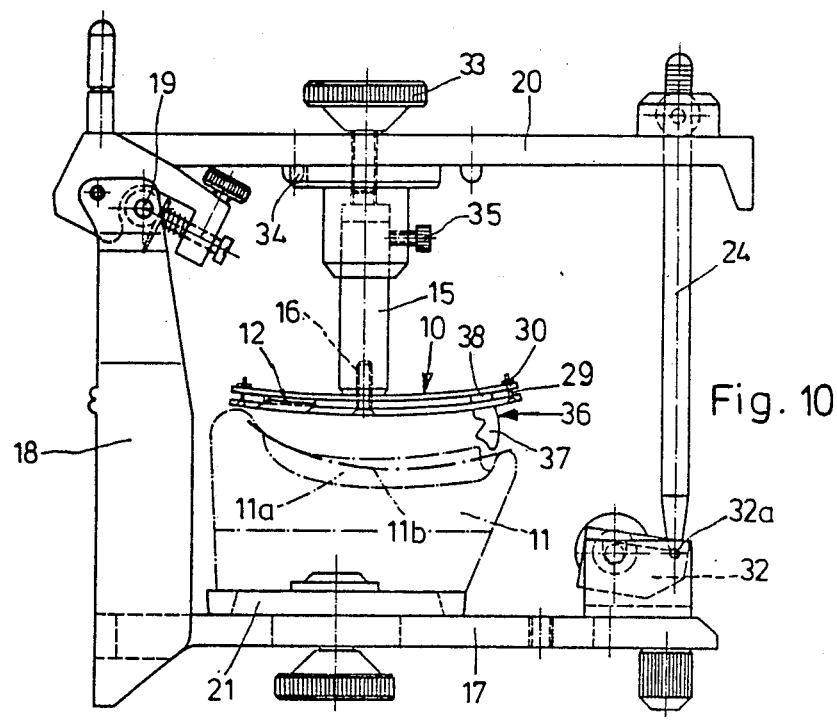
FIG. 10 is a side elevational view of the articulator apparatus with a tooth templet fixed in position on the tooth setting aid arrangement.
Figure 11:
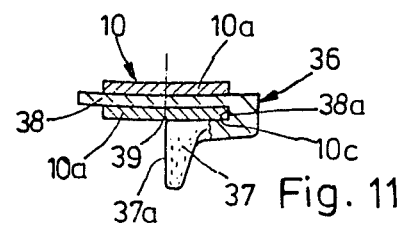
FIG. 11 is a cross-sectional view of the holder with the tooth templet inserted therein.
Figure 12:
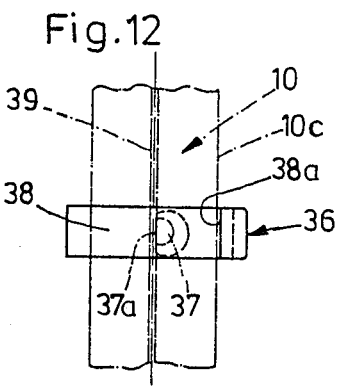
FIG. 12 is a fragmentary top plan view of the holder with the tooth templet.

Turning now to FIGS. 10 to 12 of the drawing, it may be seen therein that, for the positionally correct setting of the left or the right tooth designated as 1, there is provided a tooth templet 36 which is constituted by a pseudo tooth 37 and an insertion arm 38. The tooth templet 36 is releasably mounted on the holder 10 by the insertion arm 38 in such a manner that a mesial edge 37a of the pseudo tooth 37 is aligned with a central line 39 provided on the holder 10 and extends along the central line 39 in the sagittal direction. This tooth templet 36 renders it possible to positionally correctly set the right or left tooth 1 when a wax layer 11b is provided on the ridge 11a of the jaw model 11 in such a manner that it covers the ridge 11a in the framework of the obtained limits of the impression both as to its shape and to the area covered thereby, as a result of which the jaw model ridge 11a is covered by this wax layer 11b and is not visible.

The mesial edge 37a of the pseudo tooth 37 then constitutes an adjustment surface for the right or the left tooth 1. The mesial edge extends vertically. The central line 39 which constitutes or extends along the axis of symmetry of the denture is formed by a groove-shaped recess which is milled or otherwise provided in the lower bridge strip 10a and which extends in the longitudinal direction, and thus in the sagittal direction, of the holder 10.

The insertion arm 38 extends at an angle, preferably at a right angle, with respect to the mesial edge 37a and is configured as a flat web which extends into the space between the two bridge strips 10a of the holder 10 and is arrested in its adjusted position in the holder 10 by the screw 29 which is equipped with the knurled nut 30.

The insertion arm 38 forms an abutment edge 38a which cooperates with a longitudinal abutment edge 10c of the holder 10, especially of the lower bridge strip 10a. The cooperation of these abutment edges 38a and 10c with one another limits the insertion depth of the tooth templet 36 transversely of the longitudinal direction of the holder 10 and simultaneously assures that the mesial edge 37a is then always situated at the central line 39. In correspondence with the various dentures, the tooth templet 36 can then be infinitely shifted in the sagittal direction (in the longitudinal direction of the holder 10), while the mesial edge 37a remains constantly at the central line 39.

The pseudo tooth 37 is preferably made in one piece with the insertion arm 38 of a synthetic plastic material or metal. The pseudo tooth 37 may also have a configuration which does not correspond to that of a tooth, that is, it may be configured as a web, a boss or the like.

The tooth templet 36 is inserted for the right and left application and, depending on whether it is to be used for the right or for the left application, the insertion arm 38 points either rightwardly or leftwardly, so that two of the tooth templets 36 are to be provided for the positioning and setting of the left and right teeth 1.

To accomplish the positional adjustment, the insertion arm 38 of the tooth templet 36 is first inserted between the bridge strips 10 of the holder 10 and then the tooth templet 36 is shifted along the central line 39 into that position in which the positionally correct position corresponding to the anatomical conditions is situated.

Then, the tooth templet 36 is arrested in position by turning the knurled nut 30 in the tightening direction. After that, the holder 10, together with the tooth templet 36 is raised by the hinged arm 20.

Now, the wax layer (impression templet) 11b is applied to the jaw model ridge 11a to form the wax basis for the fabrication of the entire lower denture. Then, the hinged arm 20 is lowered again, so that the pseudo tooth 37 penetrates into the wax layer 11b. In this connection, it is advantageous to make the location of the wax layer 11b into which the pseudo tooth 37 is to penetrate weaker by a hot wax knife. Now, first the left or the right and then the right or the left tooth row including the teeth 1 to 3 can be set into the wax layer 11b.

Thereafter, the hinged arm 20 is again raised and the tooth templet 36 is removed from the holder 10. Then, the insert members 12 are inserted into the holder 10 and are posi tionally adjusted to the central fissure line, so that then the other teeth 4 to 7 can be set.

It is the purpose and advantage of the tooth templet 36, on the one hand, to make it possible to achieve an accurate setting of the teeth 1 to 3 and, on the other hand, to facilitate the adjustment of the insert members 12 to the central fissure line, inasmuch as the marking lines 13a of the insert members 12 are coincident with the central fissure line which, in turn, intersects the peak edge of the canine tooth 3. in the mesial direction as well as the centers of the rear molars in the distal direction.

The shape of the front edge of the pseudo tooth 37 corresponds to the side profile of the front surface of a lower front incisor tooth 1 and is arranged in the average correct axial inclination of a positionally correctly set front incisor tooth 1.

It is, of course, possible to adjust the marking line 13a of the insert members 12 on the Pound's line 13 instead of on the central fissure line.

While the present invention has been described and illustrated herein as embodied in a specific construction of a tooth setting aid arrangement as used with a particular articulator apparatus, it is not limited to the details of this particular construction, since various modifications and structural changes are possible and contemplated by the present invention. Thus, the scope of the present invention will be determined exclusively by the appended claims.

What is claimed is:

1. A tooth setting aid arrangement for use in a positionally correct setting of artificial teeth in a complete lower denture on a lower jaw model in accordance with a Pound's line, comprising a holder which is positionally fixable with respect to the lower jaw model and is arched along an imaginary skullcap-shaped surface with a sagittal and transversal compensation curve;

two insert members which are pivotable and shiftable on said holder within the imaginary skullcap surface as well as arrestable in selected positions thereof relative to the holder for adjustment to the Pound's line, wherein said holder is constituted by an elongated bridge member including two plate-shaped bridge elements which are juxtaposed with one another, connected to each other, and spaced from one another to jointly bound an insertion slot for said insert members, wherein each of said insert members has at least one insert arm; and wherein said holder further includes a plate-shaped distancing member interposed between said bridge elements at a central longitudinal region of the latter for forming said insertion slot between said bridge elements, and having a height corresponding to the thickness of said insert arm for alternate insertion of only one of said insert members at a time.

2. The tooth setting aid arrangement as defined in claim 1, wherein said holder is constructed for alternate releasable insertion of only one of said insertion members at a time in such a manner that said one insert member is pivotable and shiftable relative to said holder within the imaginary skullcap surface curvature as well as arrestable in a selected position thereof relative to the holder for adjustment to the respective associated left or right portion of the Pound's line.

3. The tooth setting aid arrangement as defined in claim 1, wherein said holder is constructed for simultaneous releasable insertion of both of said insertion members in such a manner that said two insert members are pivotable and shiftable relative to said holder within the imaginary skullcap surface curvature as well as arrestable in selected positions thereof relative to the holder for adjustment of each of said insert members to the respective associated left or right portion of the Pound's line 4. The tooth setting aid arrangement as defined in claim 1 for use with an articulator apparatus including a support bolt; and further comprising a rigid adapter secured to said holder and so mounted on the articulator apparatus as to determine a defined chewing plane of the arrangement with the support bolt of the articulator apparatus.

5. The tooth setting aid arrangement as defined in claim 4, wherein said holder is constituted by an elongated bridge member including two plate-shaped bridge elements which are juxtaposed with one another, connected to each other, and spaced from one another to jointly bound an insertion slot for said insert members.

6. The tooth setting aid arrangement as defined in claim 1 for use in conjunction with an articulator apparatus, and further comprising an adaptor for mounting the holder on the articulator apparatus, and a recessed head screw which mounts said holder from below on said adapter and has a recessed head which extends flush with a lower side of said holder.

7. The tooth setting aid arrangement as defined in claim 1, wherein said holder is provided with a marking line extending along a longitudinal axis of said holder.

8. The tooth setting aid arrangement as defined in claim 7, wherein said marking line is constituted by a, and bulge.

9. The tooth setting arrangement as defined in claim 7, wherein said marking line is constituted by a groove.

10. The tooth setting aid arrangement as defined in claim 1 for use with an articulator apparatus including a support bolt and an adjustment pin with a point mounted on the support bolt; and further comprising a height-adjustable adapter connected to said holder and so mounted on the articulator apparatus as to be adjustable by the adjustment pin to a chewing plane.

11. A tooth setting aid arrangement for use in a positionally correct setting of artificial teeth in a complete, lower denture on a lower jaw model in accordance with a Pound's line, comprising a holder which is positionally fixable with respect to the lower jaw model and is arched along an imaginary skullcap-shaped surface with a sagittal and transversal compensation curve;

two insert members which are pivotable and shiftable on said holder within the imaginary skullcap surface as well as arrestable in selected positions thereof relative to the holder for adjustment to the Pound's line, wherein said holder is constituted by an elongated bridge member including two plate-shaped bridge elements which are juxtaposed with one another, connected to each other, and spaced from one another to jointly bound an insertion slot for said insert members, wherein each of said insert members has at least one insert arm; and wherein said holder further includes a plate-shaped distancing member interposed between said bridge elements at a central longitudinal region of the latter for forming said insertion slot between said bridge elements and having a height corresponding to the combined thickness of said insert arms of said two insert members for simultaneous insertion of both said insert members.

12. The tooth setting aid arrangement as defined in claim 11, wherein said distancing member includes two superimposed plate-shaped distancing elements.

13. A tooth setting aid arrangement for use in a positionally correct setting of artificial teeth in a complete lower denture on a lower jaw model in accordance with a Pound's line, comprising a holder which is positionally fixable with respect to the lower jaw model and is arched along an imaginary skullcap-shaped surface with a sagittal and transversal compensation curve;

two insert members which are pivotable and shiftable on said holder within the imaginary skullcap surface as well as arrestable in selected positions thereof relative to the holder for adjustment to the Pound's line, wherein said holder is constituted by an elongated bridge member including two plate-shaped bridge elements which are juxtaposed with one another, connected to each other, and spaced from one another to jointly bound an insertion slot for said insert members, wherein each of said insert members has at least one insert arm; and wherein said holder further includes at each of the longitudinal ends of said bridge member a knurled nut and a recessed head screw which threadedly engages said knurled nut for clamping said insert arm of at least one of said insert members between said bridge elements, said screws having respective heads which extend flush with a lower side of said bridge member.

14. A tooth setting aid arrangement for use in a positionally correct setting of artificial teeth in a complete lower denture on a lower jaw model in accordance with a Pound's line, comprising a holder which is positionally fixable with respect to the lower jaw model and is arched along an imaginary skullcap-shaped surface with a sagittal and transversal compensation curve;

two insert members which are pivotable and shiftable on said holder within the imaginary skullcap surface as well as arrestable in selected positions thereof relative to the holder for adjustment to the Pound's line, wherein said holder is constituted by an elongated bridge member including two plate-shaped bridge elements which are juxtaposed with one another, connected to each other, and spaced from one another to jointly bound an insertion slot for said insert members, wherein each of said insert members includes an elongated straight portion which is adjustable to the Pound's line, and two insert arms each extending at an angle from one end of said straight portion and clampingly received in said insertion slot of said bridge member for infinite shifting and pivoting in said slot.

15. The tooth setting aid arrangement as defined in claim 14, wherein at least said straight portion of each of said insert members includes at least a region of a transparent material; and wherein a marking line which extends in the longitudinal direction of said straight portion and which is to be brought into registry with the Pound's line is provided at a lower side of said region.

16. The tooth setting aid arrangement as defined in claim 15, wherein said region is constituted by a strip of a synthetic plastic material supported on the remainder of said straight portion.

17. The tooth setting aid arrangement as defined in claim 15, wherein said straight portion is in its entirety of a transparent synthetic plastic material.

18. The tooth setting aid arrangement as defined in claim 15, wherein said marking line is constituted by a and bulge.

19. The tooth setting arrangement as defined in claim 15, wherein said marking line is constituted by a groove.

20. A tooth setting aid arrangement for use in a positionally correct setting of artificial teeth in a complete lower denture on a lower jaw model in accordance witha Pound's line, comprising a holder which is positionally fixable with respect to the lower jaw model and is arched along an imaginary skullcap-shaped surface with a sagittal and transversal compensation curve;

two insert members which are pivotable and shiftable on said holder within the imaginary skjullcap surface as well as arrestable in selected positions thereof relative to the holder for adjustment to the Pound's line, wherein said holder is provided with a central line; and further comprising at least one tooth templet including a pseudo tooth having a mesial edge, and an insertion arm connected to said pseudo tooth and releasably mountable for movement in the sagittal direction and arrestable on said holder so that said mesial edge of said pseudo tooth is aligned with said central line of said holder.

21. The tooth setting aid arrangement as defined in claim 20, wherein said mesial edge constitutes an adjustment surface for one of the left and right teeth 1.

22. The tooth setting aid arrangement as defined in claim 20, wherein said insertion arm of said tooth templet extends in one of the rightward and leftward directions from said pseudo tooth for use in the respective one of rightward and leftward applications.

23. The tooth setting aid arrangement as defined in claim 20, wherein said central line, which extends along the axis of symmetry of the denture, is formed by a groove-shaped recess which is milled into a lower bridge strip of the holder.

24. The tooth setting aid arrangement as defined in claim 20, wherein said holder includes a longitudinal abutment edge; and wherein said insertion arm of the tooth templet includes an abutment edge which cooperates with said longitudinal abutment edge of said holder to limit the insertion depth of the insertion arm and to hold the mesial edge in alignment with said central line in any adjusted position of said tooth templet in the sagittal direction.

25. The tooth setting aid arrangement as defined in claim 20, wherein said insertion arm extends at an angle with respect to said mesial edge and is insertable between bridge strips of the holder; and further comprising a screw including a knurled nut and operative for arresting said insertion arm in any position thereof which is infinitely adjusted in the sagittal direction.

26. The tooth setting aid arrangement as defined in claim 25, wherein said angle is substantially a right angle.

27. The tooth setting aid arrangement as defined in claim 20, wherein said tooth templet is of one piece.

28. The tooth setting aid arrangement as defined in claim 27, wherein said tooth templet is of a metallic material.

29. The tooth setting aid arrangement as defined in claim 27, wherein said tooth templet is of a synthetic plastic material.

* * * * *